United States Patent
Grove et al.

(10) Patent No.: US 7,504,390 B2
(45) Date of Patent: Mar. 17, 2009

(54) BENZOXAZEPINE DERIVATIVES AND THEIR USE AS AMPA RECEPTOR STIMULATORS

(75) Inventors: Simon James Anthony Grove, Newhouse (GB); Mingqiang Zhang, Kirkland (CA); Mohammad Shahid, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/924,451

(22) Filed: Oct. 25, 2007

(65) Prior Publication Data
US 2008/0139529 A1   Jun. 12, 2008

Related U.S. Application Data

(62) Division of application No. 10/480,623, filed as application No. PCT/EP02/06185 on Jun. 5, 2002, now Pat. No. 7,307,073.

(30) Foreign Application Priority Data
Jun. 11, 2001   (EP)   ................... 01202215

(51) Int. Cl.
A61K 31/55   (2006.01)
A61P 25/18   (2006.01)
A61P 25/24   (2006.01)
(52) U.S. Cl. ................................. 514/211.04
(58) Field of Classification Search ............. 514/211.04
See application file for complete search history.

(56) References Cited

U.S. PATENT DOCUMENTS 6,174,881 B1   1/2001   Borer et al.

FOREIGN PATENT DOCUMENTS

| DE | 19 54 839 A | 5/1970 |
|---|---|---|
| EP | 884 310 | 12/1998 |
| GB | 1238719 | 7/1971 |
| WO | WO 94/02475 | 2/1994 |
| WO | WO94/02475 | 2/1994 |
| WO | WO 96/20941 A | 7/1996 |
| WO | 96 38414 | 12/1996 |
| WO | WO96 38414 | 12/1996 |
| WO | 97 36907 | 10/1997 |
| WO | WO97 36907 | 10/1997 |
| WO | 99 33469 | 7/1999 |
| WO | WO99 33469 | 7/1999 |
| WO | 99 42456 | 8/1999 |
| WO | WO99 42456 | 8/1999 |
| WO | WO99/51240 | 10/1999 |
| WO | WO 99/51240 | 10/1999 |

OTHER PUBLICATIONS

Alterman et al., "Fast Microwave-Assisted Preparation of Aryl and Vinyl Nitriles and the Corresponding Tetrazoles from Organo-halides," *J. Org. Chem.* 65 (2000) 7984-7989.
Andrews et. al., "Effects of imipramine and mirtazapine on operant performance in rats," *Drug Dev. Res.* 32 (1994) 58-66.
Barn et.al., "Synthesis of Novel Analogues of the Delta Opioid Ligand SNC-80 Using AICl$_3$-Promoted Aminolysis," *Biorg. Med. Chem. Lett.* 9 (1999) 1329-34.
Bigge et al., "AMPA Receptor Agonists, Antagonists and Modulators: Their Potential for Clinical Utility," *Exp. Opin. Ther. Patents* 7 (1997) 1099-1114.
Brown et. al., "Selective Reductions. 30. Effect of Cation and Solvent on the Reactivity of Saline Borohydrides for Reduction of Carboxylic Esters. Improved Procedures for the Conversion of Esters to Alcohols by Metal Borohydrides," *J. Org. Chem.* 47 (1982) 4702-4708.
Grove et.al., "Positive Modulators of the AMPA Receptor," *Exp. Opin. Ther. Patents* 10 (2000) 1539-1548.
Hamill et. al., "Improved Patch-Clamp Techniques for High-Resolution Current Recording from Cells and Cell-Free Membrane Patches," *Pflügers Arch. 391* (1981) 85-100.

(Continued)

*Primary Examiner*—Bruck Kifle
(74) *Attorney, Agent, or Firm*—Susan Hess

(57) ABSTRACT

The present invention relates to benzoxazepine derivative having the general formula I, wherein X represents CO or SO$_2$; R$^1$, R$^2$, R$^3$ and R$^4$ are independently selected from H, (C$_{1-4}$)alkyl, (C$_{1-4}$)alkyloxy, (C$_{1-4}$)alkyloxy(C$_{1-4}$)alkyl, halogen, nitro, cyano, NR$^8$R$^9$, NR$^8$COR$^{10}$, and CONR$^8$R$^9$, R$^5$, R$^6$ and R$^7$ are independently H or (C$_{1-4}$)alkyl; R$^8$ and R$^9$ are independently H or (C$_{1-4}$)alkyl; or R$^8$ and R$^9$ form together with the nitrogen atom to which they are bound a 5- or 6-membered saturated heterocyclic ring, optionally containing a further heteroatom selected from O, S or NR$^{11}$; R$^{10}$ is (C$_{1-4}$)alkyl; R$^{11}$ is (C$_{1-4}$)alkyl; A represents the residue of a 4-7 membered saturated heterocyclic ring, optionally containing an oxygen atom, the ring being optionally substituted with 1-3 substituents selected from (C$_{1-4}$)alkyl, (C$_{1-4}$)alkyloxy, hydroxy, halogen and oxo; or a pharmaceutically acceptable salt thereof. The invention also relates to pharmaceutical compositions comprising said derivatives, and to the use of these benzoxazepine derivatives in the treatment of neurological diseases and psychiatric disorders which are responsive to enhancement of synaptic responses mediated by AMPA receptors in the central nervous system.

(I)

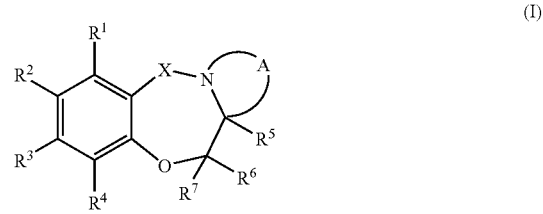

5 Claims, No Drawings

OTHER PUBLICATIONS

Ireland et al., "Application of the Swern Oxidation to the Manipulation of Highly Reactive Carbonyl Compounds," *J. Org. Chem. 50* (1985) 2198-2200.

Ito et. al., "Allosteric Potentiation of Quisqualate Receptors by a Nootropic Drug Aniracetam," *J. Physiol. 424* (1990) 533-543.

Krapcho, A.P., et. al. "Synthesis of Regioisomeric 6,9-(chlorofluoro)-Substituted Benzo[g]quinoline-5,10-diones, Benzo[g]isoquinoline-5,10-diones and 6-Chloro-9-fluorobenzo[g]quinoxaline-5,10-dione," *J. Het. Chem. 34* (1997) 27-31.

Lees, G.J., "Pharmacology of AMPA/Kainate Receptor Ligands and Their Therapeutic Potential in Neurological and Psychiatric Disorders," *Drugs 59* (2000) 33-78.

Mitsunobu, O., "The Use of Diethyl Azodicarboxylate and Triphenylphosphine in Synthesis and Transformation of Natural Products," *Synthesis 1* (1981), 1-28.

Pasquier et al., "Free and Cr(CO)$_3$-Complexed Aminophosphine Phosphinite Ligands for Highly Enantioselective Hydrogenation of α-functionalized Ketones," *Organometallics 19* (2000) 5723-5732.

Reed et. al. "Structure—Activity Relationships of Cytotoxic Cholesterol-Modified DNA Duplexes," *J. Med Chem. 38* (1995) 4587-4596.

Schoenberg A. et. al. "Palladium-Catalyzed Carboalkoxylation of Aryl, Benzyl, and Vinylic Halides," *J. Org. Chem. 39* (1974) 3318-3326.

Schoenberg et al., "Palladium-Catalyzed Amidation of Aryl, Heterocyclic, and Vinylic Halides," *J. Org. Chem. 39* (1974) 3327-3331.

Schultz et. al., "Regio- and Stereoselective Control in the Addition of Grignard Reagents to the Pyridine Ring System," *J. Org. Chem. 51* (1986) 838-841.

Schultz A G et al: "Enantioselective Method for Reductive Alkylation of Aromatic Carboxylic Acid Derivatives. Examination of the Factors that Provide Stereoselectivity"; Journal of the American Chemical Society, American Chemical Society, Washington, DC , vol. 110, No. 23, 1988, pp. 7828-7841.

Sleevi et al., "Optical Isomers of Rocastine and Close Analogues: Synthesis and H1 Antihistaminic Activity of Its Enantiomers and Their Structural Relationship to the Classical Antihistamines," *J. Med. Chem. 34* (1991) 1314-1328.

Thurston et.al., "Synthesis and Reactivity of a Novel Oxazolo[2,3-c][1,4]benzodiazepine Ring System with DNA Recognition Potential: a New Class of Anthramycins," J. Chem. Soc., Chem. Commun. (1990) 874-876.

Wolfe J.P. et. al. "Simple, Efficient Catalyst System for the Palladium-Catalyzed Amination of Aryl Chlorides, Bromides and Triflates," *J. Org. Chem. 65* (2000) 1158-1174.

Yamada et al., "Diazoxide Blocks Glutamate Desensitization and Prolongs Excitatory Postsynaptic Currents in Rat Hippocampal Neurons," *J. Physiol 458* (1992) 409-423.

Yamada, K.A., "Therapeutic Potential of Positive AMPA Receptor Modulators in the Treatment of Neurological Disease," *Exp. Opin. Invest. Drugs 9* (2000) 765-778.

BENZOXAZEPINE DERIVATIVES AND THEIR USE AS AMPA RECEPTOR STIMULATORS

RELATED APPLICATION

This application is a division of U.S. application Ser. No. 10/480,623 filed Dec. 11, 2003, which claims priority based on International Patent Application No. PCT/EP2002/06185 filed on Jun. 5, 2002, and European Patent Application No. 01202215.8, filed Jun. 11, 2001.

FIELD OF THE INVENTION

The present invention relates to benzoxazepine derivatives, to pharmaceutical compositions comprising the same and to the use of these benzoxazepine derivatives in the treatment of neurological and psychiatric diseases.

BACKGROUND OF THE INVENTION

In the mammalian central nervous system (CNS), the transmission of nerve pulses is controlled by the interaction between a neurotransmitter, that is released by a sending neuron, and a surface receptor on a receiving neuron, which causes excitation of this receiving neuron. L-Glutamate is the most abundant neuro-transmitter in the CNS. It mediates the major excitatory pathway in mammals and is referred to as an excitatory amino acid (EAA). The excitatory amino acids are of great physiological importance, playing a role in a variety of physiological processes, such as learning and memory, the development of synaptic plasticity, motor control, respiration, cardiovascular regulation and sensory perception.

The receptors that respond to glutamate are called excitatory amino acid receptors (EAA receptors). These receptors are classified into two general types: (1) "ionotropic" receptors that are directly coupled to the opening of cation channels in the cell membrane of the neurons, and (2) G-protein linked "metabotropic" receptors which are coupled to multiple secondary messenger systems that lead to enhanced phosphoinositide hydrolysis, activation of phospholipase D, increases or decreases in c-AMP formation and changes in ion channel function.

The ionotropic receptors can be pharmacologically subdivided into three subtypes, which are defined by the depolarizing actions of the selective agonists N-methyl-D-aspartate (NMDA), α-amino-3-hydroxy-5-methylisoxazole4-propionic acid (AMPA), and kainic acid (KA).

Activation of synaptic AMPA receptors mediates a voltage independent fast (~1 ms to peak response) excitatory postsynaptic current (the fast EPSC), whereas activation of synaptic NMDA receptors generates a voltage-dependent, slow (~20 ms to peak response) excitatory current. The regional distribution of AMPA receptors in the brain suggests that AMPA receptors mediate synaptic transmission in those areas likely responsible for cognition and memory.

Activation of AMPA receptors by agonists is thought to lead to a conformational change in the receptor causing rapid opening and closing of the ion channel. The extent and duration of channel activation can either be decreased by a drug, which thereby acts as a negative allosteric modulator (e.g. GYKI 52466), or it can be enhanced by a drug, which is then acting as a positive allosteric modulator.

A structural class of AMPA receptor positive modulators derived from aniracetam (e.g. CX 516) are called Ampakines. Positive modulators of the AMPA receptor can thus bind to the glutamate receptor and, upon subsequent binding of a receptor agonist, allow an ion flux through the receptor of increased duration. Defects in glutamatergic neurotransmission may be associated with many human neurological and psychiatric diseases. The therapeutic potential of positive AMPA receptor modulators in the treatment of neurological and psychiatric diseases has been reviewed by Yamada, K. A. (*Exp. Opin. Invest. Drugs*, 2000, 9, 765-777), by Lees, G. J. (*Drugs*, 2000, 59, 33-78) and by Grove S. J. A. et al. (*Exp. Opin. Ther. Patents*, 2000, 10, 1539-1548).

Various classes of compounds that increase AMPA receptor function have been recognized and were recently reviewed by Grove S. J. A. et al. (supra). N-anisoyl-2-pyrrolidinone (aniracetam; Roche) is regarded as an ampakine prototype (Ito, I. et al., *J. Physiol.* 1990, 424, 533-543), shortly thereafter followed by the discovery of certain sulphonamides (exemplified by cyclothiazide; Eli Lilly & Co) as AMPA modulators (Yamada, K. A. and Rothman, S. M., *J. Physiol.*, 1992, 458, 385-407). On the basis of the structure of aniracetam, derivatives thereof having improved potency and stability were developed by Lynch, G. S. and Rogers, G. A. as disclosed in International Patent Application WO 94/02475 (The Regents of the University of California). Additional ampakines in the form of benzoylpiperidines and pyrrolidines were subsequently disclosed in WO 96/38414 (Rogers, G. A. and Nilsson, L.; CORTEX Pharmaceuticals), followed by compounds wherein the amide function was conformationally restricted in a benzoxazine ring system, as disclosed in WO 97/36907 (Rogers G. A. and Lynch. G., The Regents of the University of California; CORTEX Pharmaceuticals), or in an acylbenzoxazine ring system, as disclosed in WO 99/51240 (Rogers G. A. and Johnström, P., The Regents of the University of California). Structurally related benzoxazine derivatives and especially 1,2,4-benzothiadiazine-1,2-dioxides, structurally derivatives of cyclothiazide™, have been disclosed in WO 99/42456 (NEUROSEARCH A/S) as positive modulators of the AMPA receptor.

Positive AMPA receptor modulators have many potential applications in humans. For example, increasing the strength of excitatory synapses could compensate for losses of synapses or receptors associated with ageing and brain disease (Alzheimer's disease, for example). Enhancing AMPA receptor-mediated activity could cause more rapid processing by multisynaptic circuitries found in higher brain regions and thus could produce an increase in perceptual motor and intellectual performance. Ampakines have further been suggested to be potentially useful as memory enhancers, to improve the performance of subjects with sensory-motor problems and of subjects impaired in cognitive tasks dependent upon brain networks utilizing AMPA receptors, in treating depression, alcoholism and schizophrenia, and in improving the recovery of subjects suffering from trauma.

It has been observed on the other hand that sustained AMPA receptor activation in experimental animals (for example, at high doses of some AMPA modulators, especially those that are potent inhibitors of receptor desensitization), can cause seizures and potentially also other proconvulsant side effects (Yamada, K. A., *Exp. Opin. Invest Drugs*, 2000, 9, 765-777). In view of the potential of excitotoxicity on AMPA receptor activation (particularly by modulators of the thiadiazide class), there remains a need for the development of modulators having a sufficient therapeutic index.

SUMMARY OF THE INVENTION

To this end the present invention provides benzoxazepine derivatives having the general formula I

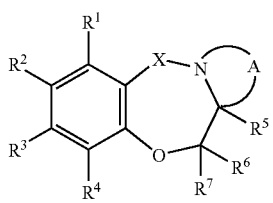

Formula I wherein
X represents CO or $SO_2$;
$R^1$, $R^2$, $R^3$ and $R^4$ are independently selected from H, $(C_{1-4})$ alkyl, $(C_{1-4})$alkyloxy, $(C_{1-4})$alkyloxy$(C_{1-4})$alkyl, $CF_3$, halogen, nitro, cyano, $NR^8R^9$, $NR^8COR^{10}$, and $CONR^8R^9$;
$R^5$, $R^6$ and $R^7$ are independently H or $(C_{1-4})$alkyl;
$R^8$ and $R^9$ are independently H or $(C_{1-4})$alkyl; or $R^8$ and $R^9$ form together with the nitrogen atom to which they are bound a 5- or 6-membered saturated heterocyclic ring, optionally containing a further heteroatom selected from O, S or $NR^{11}$;
$R^{10}$ is (C-4)alkyl;
$R^{11}$ is $(C_{1-4})$alkyl
A represents the residue of a 4-7 membered saturated heterocyclic ring, optionally containing an oxygen atom, the ring being optionally substituted with 1-3 substituents selected from $(C_{1-4})$alkyl, $(C_{1-4})$alkyloxy, hydroxy, halogen and oxo; or a pharmaceutically acceptable salt thereof; with the proviso that
the compounds of formula I wherein X is CO; each of $R^1$-$R^7$ is H, and A represents $(CH_2)_3$ or $(CH_2)_4$;
the compound of formula I wherein X is CO; $R^1$ is H; $R^2$ is methyl; each of $R^3$-$R^7$ is H; and A represents $(CH_2)_3$;
the compound of formula I wherein X is CO; $R^1$ and $R^2$ are H; $R^3$ is methyl; each of $R^4$-$R^7$ is H; and A represents $(CH_2)_3$;
the compound of formula I wherein X is CO; each of $R^1$-$R^3$ is H; $R^4$ is methyl; each of $R^5$-$R^7$ is H; and A represents $(CH_2)_3$; and
the compound of formula I wherein X is CO; each of $R^1$-$R^4$ is H; $R^5$ is methyl; $R^6$ and $R^7$ are H; and A represents $(CH_2)3$; are excluded.

The benzoxazepines for which no protection per se is sought relates to a disclosure by Schultz, A. G. et al (*J. Am. Chem Soc.* 1988, 110, 7828-7841) wherein these benzoxazepinone derivatives are described as synthetic intermediates, without any pharmacological activity.

DETAILED DESCRIPTION OF THE INVENTION

The benzoxazepines of formula I, including the prior art benzoxazepinones described by Schultz et al. (supra), have been found to be positive AMPA receptor modulators, which can be useful in the treatment of neurological and psychiatric diseases where an enhancement of synaptic responses mediated by AMPA receptors is required.

The term $(C_{1-4})$alkyl as used in the definition of formula I means a branched or unbranched alkyl group having 1-4 carbon atoms, like butyl, isobutyl, tertiary butyl, propyl, isopropyl, ethyl and methyl.

In the term $(C_{1-4})$alkyloxy, $(C_{1-4})$alkyl has the meaning as defined above.

The term $(C_{1-4})$alkyloxy$(C_{1-4})$alkyl means a $(C_{1-4})$alkyl group which is substituted with $(C_{1-4})$alkyloxy, both having the meaning as defined above.

The term halogen means F, Cl, Br or I.

In the definition of formula I $R^8$ or $R^9$ may form together with the nitrogen atom to which they are bound a 5- or 6-membered saturated heterocyclic ring, optionally containing a further heteroatom selected from O, S or $NR^{11}$. Examples of such heterocyclic ring substituents are piperidino, pyrrolidino, morpholino, N-methyl-piperazino, N-ethyl-piperazino and the like.

In the definition of formula I A represents the residue of a 4-7 membered saturated heterocyclic ring, optionally containing an oxygen atom, meaning that A is a bivalent radical containing 2-5 carbon atoms, such as ethylene, 1,3-propylene, 1,4-butylene, 1,5-pentylene, one carbon atom of which may be substituted by oxygen. Examples of 4-7 membered heterocyclic rings formed by residue A together with the nitrogen and carbon atom to which A is bonded are azetidine, pyrrolidine, piperidine, oxazolidine, isoxazolidine, morpholine, and azacycloheptane.

Preferred are the benzoxazepine derivative of formula I, wherein X is CO, which compounds are benzoxazepinones.

More preferred are the benzoxazepine derivatives of formula I, wherein X is CO and wherein $R^5$, $R^6$ and $R^7$ are H; and A represents $(CH_2)_3$.

Especially preferred are the benzoxazepine derivatives of formula I, wherein X is CO, one or more of $R^1$, $R^2$, $R^3$ and $R^4$ is halogen, preferably fluoro, and wherein $R^5$, $R^6$ and $R^7$ are H; and A represents $(CH_2)_3$.

Particular preferred compounds of the invention are:
(R)-7-Fluoro-2,3,11,11a-tetrahydro-1H,5H-pyrrolo[2,1-c][1,4]benzoxazepine-5-one;
(S)-7-Fluoro-2,3,11,11a-tetrahydro-1H,5H-pyrrolo[2,1-c][1,4]benzoxazepine-5-one
(S)-9-fluoro-2,3,11,11a-tetrahydro-1H,5H-pyrrolo[2,1-c][1,4]benzoxazepine-5-one;
(R)-9-fluoro-2,3,11,11a-tetrahydro-1H,5H-pyrrolo[2,1-c][1,4]benzoxazepine-5-one;
(S)-6Fluoro-2,3,11,11a-tetrahydro-1H,5H-pyrrolo[2,1-c][1,4]benzoxazepine-5-one.

The benzoxazepine derivatives of the invention may be prepared by methods known in the art of organic chemistry in general. More specifically such compounds can be prepared using procedures outlined by A. G. Schultz et al (*J. Am. Chem. Soc.* 1988, 110, 7828-7841) or by modification of those routes.

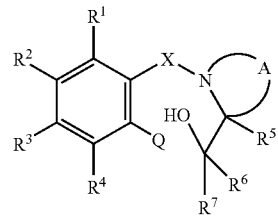

Formula II

Benzoxazepine derivatives of Formula I can for instance be prepared by cyclization of a compound according to formula II, wherein X, A and $R^1$-$R^7$ have the meaning as previously defined, any functional group with an acidic hydrogen being protected with a suitable protecting group, and wherein Q represents hydroxy, halogen or $(C_{1-4})$-alkyloxy, after which any protecting group, when present, is removed. The cyclization reaction for compounds wherein Q is halogen or $(C_{1-4})$ alkyloxy can be carried out in the presence of a base such as sodium hydride or caesium carbonate in a solvent such as dimethylformamide and at a temperature of 0-200° C., preferably 25-150° C. For compounds of formula II wherein Q is a hydroxy group, cyclization can be effected under Mitsunobu conditions (Mitsunobu, O., *Synthesis* 1981, 1) using triphenyl phosphine and a dialkyl azodicarboxylate, such as diisopropyl azodicarboxylate, in a solvent such as tetrahydrofuran.

Suitable protecting groups for functional groups which are to be temporarily protected during syntheses, are known in the art, for example from Wuts, P. G. M. and Greene, T. W.: *Protective Groups in Organic Synthesis*, Third Edition, Wiley, New York, 1999.

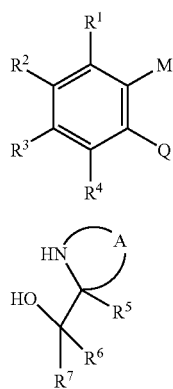

Formula III

Formula IV

Compounds of formula II can be prepared from the condensation of a compound of formula III, wherein $R^1$-$R^4$ and Q have the meaning as previously defined and M represents a carboxylic acid or an activated derivative thereof, such as a carboxylic ester or a carboxylic acid halide, preferably a chloride or a bromide, or M represents a sulfonyl halide, such as fluoride, chloride or bromide, with a compound of formula IV where $R^5$-$R^7$ and A have the meaning as previously defined.

When M represents a carboxylic acid the condensation reaction, i.e. an acylation, can be effected with the aid of a coupling reagent, such as for example carbonyl diimidazole, dicyclohexylcarbodiimide and the like, in a solvent such as dimethylformamide or dichloromethane.

When M represents a carboxylic acid halide or a sulphonyl halide the condensation with the amine derivative IV can be carried out in the presence of a base, for example triethylamine, in a solvent such as methylene chloride.

When M represents a carboxylic acid ester derivative a direct condensation with the amine derivative of Formula IV can be carried out at an elevated temperature, for example at about 50 to 200° C. This condensation can also be performed using a Lewis acid, for example aluminium trichloride as described by D. R. Barn et al (*Biorg. Med. Chem. Lett.,* 1999, 9, 1329-34).

The preparation of compounds of formula I can be performed using the methods described above by employing a one pot two step procedure, meaning that a compound of formula II, which results from a condensation reaction between a compound of formula III with a compound of formula IV, is not isolated from the reaction mixture but further treated with a base to give compounds of formula I.

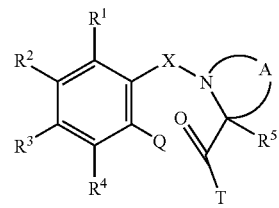

Formula V

Compounds of formula II may also be prepared from the reaction of a compound of formula V where $R^1$ to $R^5$, X and A are as defined above and T represents hydrogen, $C_{(1-4)}$alkyl, or alkyloxy, with a $C_{(1-4)}$alkylmetal reagent, for example a Grignard reagent, in a solvent such as tetrahydrofuran.

A compound of formula II where $R^6$ represents a hydrogen and $R^7$ represents a $C_{(1-4)}$alkyl group may be prepared from a compound of formula V where T represents a $C_{(1-4)}$alkyl group by a reduction, for example sodium borohydride, in a solvent such as ethanol.

A compound of formula V where X is CO and T represents an alkyloxy group may be prepared from a compound of formula III where M represents a carboxylic acid chloride and an alkanolamine imine derived from an alkyl glycolate as described by D. E. Thurston et al (*J. Chem. Soc., Chem. Commun.,* 1990, 874-876).

A compound of formula V may be prepared by coupling a compound of formula III, wherein $R^1$-$R^4$, M and Q have the meaning as previously defined, with a compound of formula VI, wherein $R^5$, A and T have the meaning as previously defined employing the methods described above for the coupling of compounds of formula III, and IV.

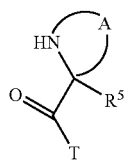

Formula VI

Compounds of formula III, IV and VI can be obtained from commercial sources, prepared by literature procedures or modifications of literature procedures known to those persons skilled in the art.

The skilled person will likewise appreciate that various compounds of Formula I can be obtained by appropriate conversion reactions of functional groups corresponding to certain of the substituents $R^1$-$R^4$.

For example, the reaction of a $(C_{1-4})$alkyl alcohol with a compound of formula I, wherein X, A and $R^5$-$R^7$ are as defined above, and wherein one of $R^1$ to $R^4$ is a leaving group such as, but not limited to, fluoro or chloro in the presence of a base such as sodium hydride gives compounds of formula I where one of $R^1$ to $R^4$ is $(C_{1-4})$alkyloxy.

Compounds of formula I where one or more of $R^1$ to $R^4$ are $CONR^8R^9$ may be prepared by conversion of a compound of formula I where one or more of $R^1$ to $R^4$ are bromo or iodo into the corresponding carboxylic acid ester using a palladium (II), for example dichlorobis(triphenylphosphine)palladium, catalysed carbonylation reaction as described by A. Schoenberg et al (*J. Org. Chem.* 1974, 39, 3318). The saponification of the ester to the carboxylic acid, using for example sodium hydroxide in tetrahydrofuran-water, and coupling of the carboxylic acid with an amine of formula NHR$^8$R$^9$ using, for example carbonyl diimidazole as coupling agent, gives compounds of formula I where one or more of R$^1$ to R$^4$ are CONR$^8$R$^9$. The carboxylic acid precursor to compounds of formula I where one or more of R$^1$ to R$^4$ are CONR$^8$R$^9$ may be prepared by the oxidation of a compound of formula I where one or more of R$^1$ to R$^4$ is a methyl group using an oxidant, for example chromium trioxide. Compounds of formula I where one or more of R$^1$ to R$^4$ are CONR$^8$R$^9$ may be prepared by a palladium (II), such as dichlorobis(triphenylphosphine)palladium, catalysed carbonylation of a compound of formula I where one or more of R$^1$ to R$^4$ are bromo or iodo in the presence of an amine of formula NHR$^8$R$^9$ using the method described by A. Schoenberg and R. F. Heck (*J. Org. Chem.* 1974, 39, 3327).

A compound of formula I where one or more of R$^1$ to R$^4$ are CN may be prepared from a compound of formula I where one or more of R$^1$ to R$^4$ is CONH$_2$ by dehydration with a dehydrating agent, for example phosphorus oxychloride. A compound of formula I where one or more of R$^1$ to R$^4$ are CN may be prepared from a compound of formula I where one or more of R$^1$ to R$^4$ is bromo or iodo using a palladium (0) catalysed cyanation reaction as described by M. Alterman and A. Hallberg (*J. Org. Chem.* 2000, 65, 7984).

A compound of formula I where one or more of R$^1$ to R$^4$ are NR$^8$R$^9$ may be prepared from a compound of formula I where one or more of R$^1$ to R$^4$ is fluoro or chloro by displacement of the halogen with an amine of formula NHR$^8$R$^9$. A compound of formula I where one or more of R$^1$ to R$^4$ are NR$^8$R$^9$ may be prepared from a compound of formula I where one or more of R$^1$ to R$^4$ is chloro, bromo or iodo by a palladium catalysted amination reaction with an amine of formula NHR$^8$R$^9$ as described by J. P. Wolfe et al (*J. Org. Chem.* 2000, 65, 1158). A compound of formula I where one or more of R$^1$ to R$^4$ are NR$^8$R$^9$ and one of R$^8$ or R$^9$ is hydrogen may be prepared from a compound of formula I where one or more of R$^1$ to R$^4$ are NR$^8$R$^9$ and both R$^8$ and R$^9$ are H by alkylation of the nitrogen atom with an alkylating agent of formula R$^9$Y where Y is a leaving group such as an alkyl or aryl sulfonate, chloro, bromo or iodo. A compound of formula I where one or more of R$^1$ to R$^4$ are NR$^8$R$^9$ and both R$^8$ and R$^9$ are H may be prepared from a compound of formula I where one or more of R$^1$ to R$^4$ are nitro by a reduction for example a palladium catalysed reduction with hydrogen. A compound of formula I where one or more of R$^1$ to R$^4$ are NR$^8$COR$^{10}$ may be prepared from a compound of formula I where one or more of R$^1$ to R$^4$ are NHR$^8$ by treatment with an acylating agent such as a C$_{(1-5)}$acid chloride or anhydride, for example acetic anhydride, in a solvent, for example pyridine.

Treatment of a compound of formula I, where A represents a residue of a 4-7 membered saturated heterocyclic ring substituted with 1-3 hydroxy groups, with a base, such as sodium hydride, in a solvent, such as tetrahydrofuran, with an alkylating agent of formula C$_{(1-4)}$alkyl where Y is defined as above gives a compound of formula I where A represents a residue of a 4-7 membered saturated heterocyclic ring optionally substituted with 1-3 alkyloxy groups.

In a compound of formula I, where A represents a residue of a 4-7 membered saturated heterocyclic ring substituted with 1-3 hydroxy groups, the hydroxy group(s) can be substituted by halogen by treatment with a halogenating reagent such as (diethylamino)sulfur trifluoride (DAST) or with the carbon tetrahalide-triphenyl-phosphine combination.

Similarly, a compound of formula I where A represents a residue of a 4-7 membered saturated heterocyclic ring optionally substituted with 2 halogen groups at the same carbon atom may be prepared from the corresponding oxo-derivative by treatment with a halogenating agent, such as DAST.

The oxidation of compound of formula I, where A represents a residue of a 4-7 membered saturated heterocyclic ring optionally substituted with 1-3 hydroxy groups, with an oxidising agent, such as in the Swern oxidation as described by R. E. Ireland and D. W. Norbeck (*J. Org. Chem.* 1985, 50, 2198-2200), gives compounds of formula I where A represents a residue of a 4-7 membered saturated heterocyclic ring optionally substituted with 1-3 oxo groups.

The benzoxazepine derivatives of Formula I and their salts contain at least one centre of chirality, and exist therefore as stereoisomers, including enantiomers, and when appropriate, diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley). Specific methods applicable for the stereoselective preparation of benzoxazepine derivatives of this invention are those described by Schultz, A. G. et al. (*J. Am. Chem Soc.* 1988, 110, 7828-7841).

Pharmaceutically acceptable salts may be obtained by treating a free base of a compound according to formula I with a mineral acid such as hydrochloric acid, hydrobromic acid, phosphoric acid and sulphuric acid, or an organic acid such as for example ascorbic acid, citric acid, tartaric acid, lactic acid maleic acid, malonic acid, fumaric acid, glycolic acid, succinic acid, propionic acid, acetic acid, methane sulphonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a benzoxazepine derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The benzoxazepines of the invention are AMPA receptor stimulators, as can be determined by an increase in steady state current induced by application of glutamate in a conventional whole cell patch clamp method when a benzoxazepine of the invention is present (see Example 30 and Table I). The compounds may be used in the treatment of neurological and psychiatric diseases where an enhancement of synaptic responses mediated by AMPA receptors is required, such as neuro-degenerative disorders, cognitive or memory dysfunction, memory and learning disorders such as can result from ageing, attention disorder, trauma, stroke, epilepsy, Alzheimer's disease, depression, schizophrenia, psychotic disorders, anxiety, sexual dysfunctions, autism, or a disorder or disease resulting from neurotic agents or substance abuse, and alcohol intoxication.

The compounds of the invention may be administered for humans in a dosage of 0.001-50 mg per kg body weight, preferably in a dosage of 0.1-20 mg per kg body weight.

The invention is illustrated by the following Examples.

EXAMPLE 1

(R)-7-Fluoro-2,3,11,11a-tetrahydro-1H,5H-pyrrolo
[2,1-c][1,4]benzoxazepine-5-one

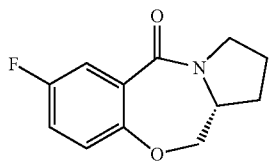

To a solution of 2,5-difluorobenzoic acid (1.0 g; 6.325 mmol) in dimethylformamide (5 ml) was added 1,1'- carbonyldiimidazole (1.07 g; 6.64 mmol) and the solution stirred at room temperature for 1 h, followed by the addition of (R)-(−)-2-pyrrolidinemethanol (0.655 ml; 6.64 mmol). The reaction was stirred at room temperature overnight whereupon 60% sodium hydride in mineral oil (0.507 g; 12.7 mmol) was carefully added and the mixture was heated to 120° C. for 2 h. The reaction was cautiously diluted with water and extracted with ethyl acetate and the organic layer washed with water then dried ($Na_2SO_4$) and evaporated to give the crude product. Trituration with ether and filtration afforded the title compound (0.29 g). M.p.: 85-86° C.; EIMS: m/z=222.2 $[M+H]^+$

EXAMPLE 2

(S)-7-Fluoro-2,3,11,11a-tetrahydro-1H,5H-pyrrolo
[2,1-c][1,4]benzoxazepine-5-one

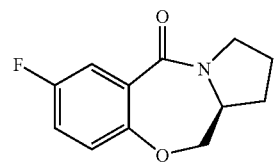

The title compound was prepared following the method of Example 1 using (S-(+)-2-pyrrolidinemethanol. M.p.: 80-82° C.; EIMS: m/z=222.2 $[M+H]^+$

EXAMPLE 3

The procedure described under Example 1 was further used to prepare the following compounds:

3A: (R)-9-Fluoro-2,3,11,11a-tetrahydro-1H,5H-pyrrolo[2, 1c][1,4]benzoxazepine-5-one was obtained from 2,3-difluorobenzoic acid and (R)-(−)-2-pyrrolidinemethanol. M.p.: 94-95° C.; EIMS: m/z=222.1 $[M+H]^+$ 3B: (S)-9-Fluoro-2,3,11,11a-tetrahydro-1H,5H-pyrrolo[2,1-c][1,4]benzoxazepine-5-one was obtained from 2,3-difluorobenzoic acid and (S)-(+)-2-pyrrolidinemethanol. M.p.: 92-93° C.; EIMS: m/z=222.2 $[M+H]^+$ 3C: (R)-8-Trifluoromethyl-2,3,11,11a-tetrahydro-1H,5H-pyrrolo[2,1-c][1,4]benzoxazepine-5-one was obtained from 2-fluoro-4-trifluoromethylbenzoic acid and (R)-(−)-2-pyrrolidinemethanol. M.p.: 92-94° C.; EIMS: m/z=222.2 $[M+H]^+$ 3D: (S)-8-Trifluoromethyl-2,3,11,11a-tetrahydro-1H,5H-pyrrolo[2,1c]-[4,1]benzoxazepine-5-one was obtained from 2-fluoro-4-trifluoromethylbenzoic acid and (S)-(+)-2-pyrrolidinemethanol. M.p., 95-96,° C.; EIMS: m/z=272.1 $[M+H]^+$ 3E: (R)-6-Fluoro-2,3,11,11a-tetrahydro-1H,5H-pyrrolo[2,1-c[]1,4]benzoxazepine-5-one was obtained from 2,6-difluorobenzoic acid and (R)-(−)-2-pyrrolidinemethanol, m.p., 146-148° C.; EIMS: m/z=222.2 $[M+H]^+$ 3F: (S)-8-chloro-2,3,11,11a-tetrahydro-1H,5H-pyrrolo[2,1-c][1,4]benzoxazepine-5-one was obtained from 2,4-dichlororobenzoic acid and (S)-(+)-2-pyrrolidinemethanol. M.p., 105-106° C.; EIMS: m/z=238.2 $[M+H]^+$ 3G: (S)-7-chloro-2,3,11,11a-tetrahydro-1H 5H-pyrrolo[2,1-c][1,4]benzoxazepine-5-one was obtained from 2,5-dichlororobenzoic acid and (S)-(+)-2-pyrrolidinemethanol. M.p., 124-126° C.; EIMS: m/z=238 $[M+H]^+$ 3H: (±)-3-Fluoro-6,6a,7,8,9, 10-hexahydro-12H-pyrrolo[2, 1-c][1,4]benzoxazepine-12was obtained from 2,5-difluorobenzoic acid and 2-piperidinemethanol and isolated as a gum. EIMS: m/z=236 $[M+H]^+$ 3I: (R)-7-Bromo-2,3,11,11a-tetrahydro-1H,5H-pyrrolo[2,1-c][1,4]benzoxazepine-5-one was obtained from 5-bromo-2-chlorobenzoic acid and (R)-(−)-2-pyrrolidinemethanol. M.p. 115-116° C.; EIMS: m/z=284 [M+H]$^+$ 3J: (S)-7-Bromo-2,3,11,11a-tetrahydro-1H,5H-pyrrolo[2,1-c][1,4]benzoxazepine-5-one was obtained from 5-bromo-2-chlorobenzoic acid and (S)-(+)-2-pyrrolidinemethanol. M.p. 115-116° C.; EIMS: m/z=284 [M+H]$^+$ 3K: (R)-7-Nitro-2,3,11,11a-tetrahydro-1H,5H-pyrrolo[2,1-c][1,4]benzoxazepine-5-one was obtained from 5-nitro-2-chlorobenzoic acid and (R)-(−)-2-pyrrolidinemethanol. M.p. 169-170° C.; EIMS: m/z=249 [M+H]$^+$ 3L: (S)-7-Nitro-2,3,11,11a-tetrahydro-1H,5H-pyrrolo[2,1-c][1,4]benzoxazepine-5-one was obtained from 5-nitro-2-chlorobenzoic acid and (S)-(+)-2-pyrrolidinemethanol. M.p. 170-171° C.; EIMS: m/z=249 [M+H]$^+$

EXAMPLE 4

(R)-8-chloro-2,3,11,11a-tetrahydro-1H,5H-pyrrolo[2,1-c][1,4]benzoxazepine-5-one

To a solution of 2,4-dichlorobenzoic acid (1.21 g; 6.325 mmol) in dimethylformamide (5 ml) was added 1,1'-carbonyldiimidazole (1.07 g; 6.64 mmol) and the solution stirred at room temperature for 1 h before the addition of (R)-(−)-2-pyrrolidinemethanol (0.655 ml; 6.64 mmol). The reaction was stirred at room temperature overnight then the solvent was removed in vacuo and the residue purified by chromatography on silica (eluting with 5% methanol in dichloromethane) to give the intermediate amide which was not characterised but taken directly onto the next step. To a solution of this amide (0.6 g), in dimethylformamide was added caesium carbonate (1.5 g). The mixture was heated at 150° C. for 2 h, then cooled to room temperature. The reaction was diluted with water and extracted with ethyl acetate. The organic layer was washed with water and dried ($Na_2SO_4$). Evaporation of the solvent and the solvent removed. The crude product was purified by chromatography on silica (eluting with 5% methanol in dichloromethane). The resulting clear oil crystallised on standing and was triturated with heptane. Filtration afforded the title compound (0.22 g). M.p., 92-94° C.; EIMS: m/z=238.1 [M+H]$^+$

EXAMPLE 5

The procedure described under Example 4 was further used to prepare:

(S)-8-fluoro-2,3,11,11a-tetrahydro-1H,5H-pyrrolo[2,1-c][1,4]benzoxazepine-5-one was obtained from 2,4-difluorobenzoic acid and (S)-(+)-2-pyrrolidinemethanol. M.p., 75-76° C.; EIMS: m/z=222.2 [M+H]$^+$

EXAMPLE 6

(±)-3-Trifluoromethyl-6,6a,7,8,9,10-hexahydro12H-pyrrolo[2,1-c][1,4]benzoxazepine-12-one To a solution of 2-fluoro-4-(trifluoromethyl)-benzoic acid (1.31 g; 6.325 mmol) in dimethylformamide (5 mL) was added 1,1'-carbonyldiimidazole (1.08 g; 6.64 mmol) and the solution stirred at room temperature for 1 h, whereupon 2-piperidinemethanol (0.765 g; 6.64 mmol) was added. The reaction was stirred at room temperature overnight then caesium carbonate (4.12 g) was added and the mixture heated to 120° C. for 4 h. Diluted with water the product was extracted into ethyl acetate and washed with water. Organic layer was dried ($Na_2SO_4$) and evaporation of the solvent in vacuo gave the crude product which crystallised from 5% ether in heptane to give the title compound (0.83 g). M.p.: 103-104° C.; EIMS: m/z=286 [M+H]$^+$

EXAMPLE 7

The procedure described under Example 6 was further used to prepare the following compounds:

7A: (±)-4Fluoro-6,6a,7,8,9,10-hexahydro-12H-pyrido[2,1-c][1,4]benzoxazepine-12-one was obtained from 2,3-difluorobenzoic acid and 2-piperidinemethanol as a gum. EIMS: m/z=235.8 [M+H]$^+$ 7B: (±)-3-Fluoro-6,6a,7,8,9,10-hexahydro-12H-pyrido-[2,1-c][1,4]benzoxazepine-12-one was obtained from 2,4-difluorobenzoic acid and 2-piperidinemethanol as a gum, EIMS: m/z=236.2 [M+H]$^+$ 7C: (±)-1-Fluoro-6,6a,7,8,9 10-hexahydro-12H-pyrido[2,1-c][1,4]benzoxazepine-12-one was obtained from 2,6-difluorobenzoic acid and 2-piperidinemethanol. M.p., 133-134° C.; EIMS: m/z=236.2 [M+H]$^+$

EXAMPLE 8

(S)-9-Chloro-2,3,11,11a-tetrahydro-1H,5H-pyrrolo[2,1-c][1,4]benzoxazepine-5-one

To a solution of 3-chloro-2-fluorobenzoyl chloride (2.2 g; 11.4 mmol) in dimethylformamide (5 ml) was added triethylamine (1.7 mL; 11.7 mmol) and (S)-(+)-2-pyrrolidinemethanol (1.13 mL; 11.4 mmol). The mixture was stirred for 1 h then caesium carbonate (7.4 g; 22.7 mmol) was added and the reaction heated at 120° C. for 5 hours. The reaction was cooled to room temperature then diluted with water and extracted with ethyl acetate The organics were washed with water and dried ($Na_2SO_4$) evaporated in vacuo. The crude product was purified by chromatography on silica (eluting with 5% methanol in dichloromethane). On removal of solvent the pure amide crystallised and heptane/ether was added and the title compound collected (0.26 g). M.p., 89-90° C.; EIMS: m/z=238 [M+H]$^+$

EXAMPLE 9

The procedure described under Example 8 was further used to prepare the following compounds:

9A: (S)-6-Fluoro-2,3,11,11a-tetrahydro-1H,5H-pyrrolo[2,1-c][1,4]benzoxazepine-5-one was obtained from 2,6-difluorobenzoyl chloride and (S)-(+)-2-pyrrolidine-methanol. M.p., 149-150° C.; EIMS: m/z=222.2 [M+H]$^+$ 9B: (S)-6-Chloro-2,3,11,11a-tetrahydro-1H,5H-pyrrolo[2,1-c][1,4]benzoxazepine-5-one was obtained from 2,6-dichlorobenzoyl chloride and (S)-(+)-2-pyrrolidinemethanol. M.p., 113-115° C.; EIMS: m/z=238.2 [M+H]$^+$ 9C: (S)-6-Trifluoromethyl-2,3,11,11a-tetrahydro-1H,5H-pyrrolo[2,1-c][1,4]benzoxazepine-5-one was obtained from 2-fluoro-6-trifluoromethylbenzoyl chloride and (S)-(+)-2-pyrrolidinemethanol. M.p., 175-176° C.; EIMS: m/z=272.2 [M+H]$^+$ 9D: (S)-7-Trifluoromethyl-2,3,11,11a-tetrahydro-1H,5H-pyrrolo[2,1-c][1,4]benzoxazepine-5-one was obtained from 2-fluoro-5-trifluoromethylbenzoyl chloride and (S)-(+)-2-pyrrolidinemethanol. M.p., 120-121° C.; EIMS: m/z=272.4 [M+H]$^+$ 9E: (S)-8,9-Difluoromethyl-2,311,11a-tetrahydro-1H5H-pyrrolo[2-c][1,4]benzoxazepine-5-one was obtained from 2,3,4-trifluorobenzoic acid and (S)-(+)-2-pyrrolidinemethanol. M.p., 142-143° C.; EIMS: m/z=272.2 [M+H]+

EXAMPLE 10

(S)-2,3,11,11,a-tetrahydro-1H,5H-pyrrolo[2,1-c][5,1,4]benzthiaoxazepine-5-dioxide To a solution of 2-fluorobenzenesulfonyl chloride (1.7 g; 8.8 mmol) in methylenechloride (50 mL) was added triethylamine (1.8 mL; 12.9 mmol) and (S)-(+)-2-pyrrolidinemethanol (1.07 mL; 10.7 mmol). The mixture was stirred for 7 hours then diluted with methylene chloride and washed with 2M hydrochloric acid and the organic layer was dried (Na$_2$SO$_4$). Evaporation of the solvent gave the crude sulfonamide which was taken up in 100 ml of dimethylformamide and 1.0 g of 60% sodium hydride in mineral oil was added. The mixture was stirred overnight and then evaporation of the solvent and aqueous work up followed by purification by chromatography on silica (eluting with ethyl acetate) afforded the title compound as a gum; $^1$H NMR (400 MHz; CDCl$_3$) δ 1.93-2.00 (m, 3H), 2.20-2.27 (m, 1H), 3.05-3.09 (m, 1H), 3.58-3.63 (m, 1H), 3.94 (dd, 1H), 4.18-4.21 (m, 1H), 4.76 (dd, 1H), 7.09 (dd, 1H), 7.19 (dd, 1H), 7.43 (dd, 1H), 7.84 (dd, 1H); EIMS: m/z=240 [M+H]+

EXAMPLE 11

(S)-8-Methoxy-2,3,11,11a-tetrahydro-1H,5H-pyrrolo[2,1-c][1,4]benzoxazepine-5-one A solution of (S)-8-fluoro-2,3,11,11a-tetrahydro-1H,5H-pyrrolo[2,1-c][1,4]-benzoxazepine-5-one (0.5 g; 2.14 mmol), prepared as described in Example 5A, and sodium methoxide (0.244 g; 4.52 mmol) in dimethylformamide (2 mL) was heated at 110° C. for 3 h. The reaction was diluted with water and extracted with ethyl acetate and the organic layer washed with water then dried (Na$_2$SO$_4$) and evaporated in vacuo. The crude product was purified by chromatography on silica (eluting with 5% methanol in dichloromethane) to give the title product, m.p. 104-106° C.; EIMS: m/z=234 [M+H]+

EXAMPLE 12

(S)-8-(1-Pyrrolo)-2,3,11,11a-tetrahydro-1H,5H-pyrrolo[2,1-c][1,4]benzoxazepine-5-on hydrochloride salt A solution of (S)-8-fluoro-2,3,11,11a-tetrahydro-1H,5H-pyrrolo[2,1-c][1,4]-benzoxazepine-5-one (0.5 g; 2.14 mmol), prepared as described in Example 5A, in pyrrolidine (1 ml) was heated under reflux for 4 h. Reaction was diluted with water and extracted with ethyl acetate and washed with water then dried (Na$_2$SO$_4$) and evaporated in vacuo. The crude product was chromatographed on silica (eluting with 5% methanol in dichloromethane) and then crystallised from 5% dichloromethane in ether. The pure product was dissolved in dichloromethane and converted to the hydrochloride salt with HCl in ether then ether was added to precipitate the title product (0.18 g). M.p.,169-176° C.; EIMS: m/z=273 [M+H]+

EXAMPLE 13

(S)-7-amino-2,3,11,11a-tetrahydro-1H,5H-pyrrolo[2,1-c][1,4]benzoxazepine-5-one

A solution of (S)-7-nitro-2,3,11,11a-tetrahydro-1H,5H-pyrrolo[2,1-c][1,4]benzoxazepine-5-one (7.4 g), prepared as described in Example 3L, in ethanol (100 ml) and methanol (50 ml) was hydrogenated over 10% palladium on activated carbon under 2 bar hydrogen, until the uptake of hydrogen ceased. The mixture was filtered to remove the catalyst and evaporated to dryness in vacuo. The crude product was passed through a short silica column (eluting with 10% methanol in dichloromethane) to give the title product (6.1 g). EIMS: m/z=219 [M+H]+

EXAMPLE 14

(S)-N-(2,3,11,11a-tetrahydro-5-oxo-1H,5H-pyrrolo[2,1-a][1,4]benzoxazepin-7-yl)-acetamide

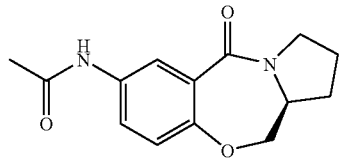

A solution of the material from Example 13 (2.29 mmol) and acetic anhydride (0.237 ml; 2.5 mmol) in pyridine (5 ml) was allowed to stand at room temperature overnight. Reaction diluted with water and extracted into ethyl acetate, washed with water then dried (Na$_2$SO$_4$) and evaporated in vacuo. The crude product was crystallised from 5% dichloromethane in heptane to give the title product (140 mg). M.p. 185-187° C.; EIMS: m/z=261 [M+H]+

EXAMPLE 15

(S)-7-(Piperidinocarbonyl)-2,3,11,11a-tetrahydro-1H,5H-pyrrolo[2,1-c][1,4]benzoxazepine-5

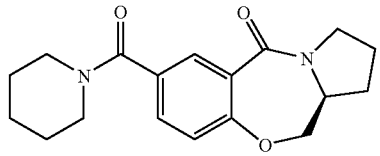

A solution of (S)-7-Bromo-2,3,11,11a-tetrahydro-1H,5H-pyrrolo[2,1-c][1,4]-benzoxazepine-5-one (0.56 g; 2 mmoles), prepared as described in Example 3J, together with piperidine (2 ml) and dichlorobis(triphenylphosphine)palladium (II) (63 mg) was heated at 110° C. under an atmosphere of carbon monoxide overnight. Evaporation, partitioning of residue between water and dichloromethane and evaporation of the organic layer followed by chromatographic purification eluting with 5% methanol in dichloromethane and crystallisation from ethyl acetate/petroleum ether gave 400 mg of the title product. M.p. 140-140.5° C.; EIMS: m/z=315 [M+H]$^+$

EXAMPLE 16

The procedure described under Example 15 was further used to prepare the following compounds:
16A: (S)-7-(morpholinocarbonyl)-2,3,11,11a-tetrahydro-1H,5H-pyrrolo[2,1-c][1,4]-benzoxazepine-5-one The title compound was obtained using morpholine in place of piperidine as the reactant. M.p. 158-161° C.; EIMS: m/z=317 [M+H]$^+$ 16B: (S)-7-(N-ethylpiperazinocarbonyl)-2,3,11,11a-tetrahydro-1H,5H-pyrrolo[2,1-c]-[1,4]benzoxazepine-5-one hydrochloride salt The title compound was obtained using N-ethylpiperazine in place of piperidine as the reactant and isolated as the hydrochloride salt by crystallisation from acetone-ether. M.p.>200° C.; EIMS. m/z=344 [M+H]$^+$

EXAMPLE 17

17A: (S)-7-(aminocarbonyl)-2,3,11,11a-tetrahydro-1H,5H-pyrrolo[2,1-c][1,4]benzoxazeline-5-one To a solution of (S)-7-Bromo-2,3,11,11a-tetrahydro-1H,5H-pyrrolo[2,1-c][1,4]-benzoxazepine-5-one (5 g; 17.76 mmol), prepared as described in Example 3J, in dimethylsulfoxide (80 ml) was added palladium acetate (225 mg; 1 mmol), 1,3-bis-(diphenylphosphino)propane (413 mg; 1 mmol), triethylamine (5 ml; 36 mmol) and methanol (4 ml). After stirring under argon until all solids had dissolved the reaction vessel was purged several times with carbon monoxide and placed under an atmosphere of carbon monoxide (balloon). The mixture was then heated to 100° C. and stirred overnight. Further portions of palladium acetate (0.50 mmol) and 1,3-bis-(diphenylphosphino)propane (0.50 mmol) were added and the mixture stirred at 100° C. for a further 6 h. After cooling water (200 ml) was added and the aqueous solution was extracted with three 75 ml portions of ethyl acetate. The combined extracts were dried (Na$_2$SO$_4$) and solvent evaporated under reduced pressure. The resulting brown oil was purified by column chromatography eluting with ethyl acetate. Further purification by recrystallisation from diethyl ether gave methyl (S)-2,3,11,11a-tetrahydro-1H,5H-pyrrolo[2,1-c][1,4]benzoxazepine-5-one-7-carboxylate (3.13 g) as a white crystalline solid To a solution of this methyl ester (2.54 g; 9.73 mmol) in methanol (40 ml) was added 4M sodium hydroxide (12 ml). The mixture was heated under reflux for 1.5 h and then allowed to cool to room temperature. The methanol was evaporated under reduced pressure and the aqueous solution was acidified with aqueous 1 M HCl. The resulting precipitate was filtered off and dried under vacuum to give (S)-2,3,11,11a-tetrahydro-1H ,5H-pyrrolo[2,1-c][1,4]benzoxazepine-5-one-7-carboxylic acid (2.39 g) as an off white solid.

A solution of the above carboxylic acid derivative (2.38 g; 9.64 mmol) in thionyl chloride (10 ml) was heated under reflux for 1.5 h. The excess thionyl chloride was evaporated under reduced pressure to giving (S)-2,3,11,11a-tetrahydro-1H,5H-pyrrolo[2,1-c][1,4]benzoxazepine-5-one-7-carboxylic acid chloride (2.56 g) as a pale yellow solid.

A solution of the acid chloride (1.02 g; 3.85 mmol) in dichloromethane (8 ml) was added to a stirred solution of 38% aqueous ammonia (5 ml). After stirring for 20 min the dichloromethane was removed under reduced pressure. The white precipitate that had formed was collected by filtration and dried under vacuum to give the title compound (886 mg) as a white solid. M.p. 287-290° C.; EIMS: m/z=247.4 [M+H]$^+$ 17B: (R)-7-(Aminocarbonyl)-2,3,11,11a-tetrahydro-1H,5H-pyrrolo[2 1-c][1,4]benzoxazepine-5-one was obtained following the method of Example 18A starting from the material prepared in Example 3I. M.p. 290-295° C. EIMS: m/z=247.2 [M+H]$^+$

EXAMPLE 18

(R)-7-(Methylaminocarbonyl)-23,11,11a-tetrahydro-1H,5H-pyrrolo[2,1-c][1,4]benzoxazepine-5-one A solution of (R)-2,3,11,11a-tetrahydro-1H,5H-pyrrolo[2,1-c][1,4]benzoxazepine-5-one-7-carboxylic acid chloride (0.330 g; 1.24 mmol), prepared as described in Example 17A, starting from the material described in Example 3I in dichloromethane (3 ml) was added dropwise to a stirred 10% solution of methylamine in tetrahydrofuran. The mixture was stirred at room temperature for a further 1 h and then evaporated to dryness under reduced pressure. The residue was taken up in dichloromethane (20 mL) and washed with 0.5M HCl (2×20 mL). The dichloromethane layer was dried (MgSO$_4$) and solvent evaporated under reduced pressure. Recrystallisation of the crude product from ethylacetate/diethylether gave the title compound (0.262 g) as a white solid. M.p. 186-189° C.; EIMS: m/z=261.0 [M+H]$^+$

EXAMPLE 19

(R)-7-Cyano-2,3,11,11a-tetrahydro-1H5H-pyrrolo[2,1-c][1,4]benzoxazepine-5-one

To a stirred solution of the material prepared in Example 17B (1.57 mmol) in dimethylformamide (5 ml) under a nitrogen atmosphere was added phosphorous oxychloride (731 µl; 7.85 mmol). The mixture was stirred for 0.5 h at 80° C. After cooling water (20 ml) was added and upon stirring a white precipitate formed. The precipitate was collected by filtration, washed with water and dried under vacuum to give the title compound (261 mg). M.p. 164-165° C.; EIMS: m/z=229.0 [M+H]$^+$

EXAMPLE 20

20A: (11R, 11aS)-11-Ethyl-2,3,11,11a-tetrahydro-1H,5H-pyrrolo[2,1-c][1,4]benzoxazepine-5-one To 2-chlorobenzoic acid (10 g; 63.9 mmol) in dimethylformamide (100 ml) under nitrogen was added carbonyldiimidazole (10.9 g; 67.1 mmol) and the solution stirred for 1 h at room temperature. (S)-(+)-2-pyrrolidinemethanol (7.56 ml, 76.6 mmol) was added and the mixture stirred at 40° C. for 18 h. The solvent was removed under reduced pressure and the crude product purified by chromatography on silica (eluting with 50% to 75% ethyl acetate in heptane) to afford (S)-1-(2-chlorobenzoyl)-2-pyrrolidinemethanol (10.2 g), which was used directly in the next step.

Tetrahydrofuran (24 ml) was cooled to −60° C. with stirring and oxalyl chloride (1.15 ml, 13.2 mmol) was added. Dimethylsulfoxide (0.98 ml, 13.8 mmol) was then added dropwise. The mixture was stirred for 20 minutes, then a solution of 1-(2-chlorobenzoyl)-2-pyrrolidinemethanol (3.0 g, 12.5 mmol) in tetrahydrofuran (24 ml) was added dropwise over 15 minutes. After a further 15 minutes, the mixture was treated with triethylamine (7.0 ml, 50.1 mmol). The mixture was warmed briefly to 0° C. before re-cooling to −78° C. Ethylmagnesium bromide (3.0 M in diethyl ether; 16.7 ml, 50.1 mmol) was added dropwise to the vigorously stirred reaction mixture. The reaction was warmed to −40° C. for 1 h, re-cooled to −78° C. and then cautiously treated with ethanol (5 ml) followed by saturated ammonium chloride solution. The mixture was allowed to warm to room temperature, and then extracted with ethyl acetate (ca. 150 ml). The organic layer was dried (Na$_2$SO$_4$) and concentrated to afford crude (2S,αRS)-1-(2-chlorobenzoyl)-α-ethyl-2-pyrrolidinemethanol as a mixture of diastereoisomers. The crude product was dissolved in dimethylformamide (100 ml) under nitrogen. Sodium hydride (60% dispersion in mineral oil; 1.0 g, 25.0 mmol) was added, portionwise. The reaction was stirred at room temperature for 30 minutes and then heated to 120° C. for 5 h, after which the temperature was reduced to 80° C. for a further 16 h. The reaction was allowed to cool to room temperature and then quenched with methanol (10 ml) and stirred for 10 minutes. The solvents were removed under reduced pressure. The residue was taken up in water (50 ml) and extracted with dichloromethane (2×50 ml) to afford the product as a crude mixture of diastereoisomers (ratio approx. 30:70). Flash chromatography on silica (eluting with 0% to 80% ethyl acetate in heptane) afforded the title compound (80 mg) as a colourless oil; $^1$H NMR (400 MHz; CDCl$_3$) δ 4.24 (1H, dt, J 10.5, 2.3 Hz, 11-H); EIMS: m/z=232 [M+H]$^+$ 20B: (11S. 11aS)-11-Ethyl-2,3,11,11a-tetrahydro-1H,5H-pyrrolo[2,1-c][1,4]benzoxazepine-5-one Further elution of the mixture prepared in Example 20A gave the title compound, which was recrystallised from ethyl acetate/heptane to afford a white crystaline product. M.p. 118-119° C.; $^1$H NMR (400 MHz; CDCl$_3$) δ 4.04 (1H, td, J 9.8, 2.5 Hz, 11-H); EIMS: m/z=232 [M+H]$^+$.

EXAMPLE 21

21A: (6RS,6aSR)-2-Bromo6-methyl-6,6a,7,8,9,10-hexahydro-12H-pyrido[2,1-c][1,4]-benzoxazepine-12-one

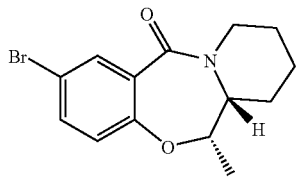

The title compound was prepared following the method of Example 20A, using 5-bromo-2-chlorobenzoic acid, (RS)-2-piperidinemethanol and methylmagnesium bromide. M. p. 105-106° C.; EIMS: m/z=312 [M+H]$^+$ 21B: (6RS,6aRS)-2-Bromo-6-methyl-6,6a,7,8,9,10-hexahydro-12H-pyrido[2,1-c][1,4]-benzoxazepine-12-one This enantiomer was obtained on further elution of the mixture obtained from Example 21A gave the title product, M. p. 105-107° C.; EIMS: m/z=312 [M+H]$^+$.

EXAMPLE 22

6,6a-Dihydro-12H-Morpholino[3,4-c][1,4]benzoxazepin-12-one

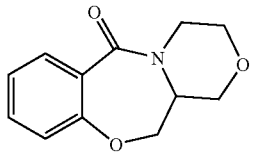

A solution of morpholine-3-carboxylic acid (4.035 g; 30.8 mmol) in ethanol (250 ml) was saturated with gaseous HCl, then stirred for a week. The solvent was evaporated and the residue taken up in water and made basic (pH ~10) with sodium hydrogen carbonate and sodium carbonate. The mixture was then extracted with dichloromethane (7×), the combined extracts dried (Na$_2$SO$_4$) and the solvent evaporated to give ethyl morpholine-3-carboxylate (746 mg). EIMS: m/z=160.4 [M+H]$^+$. This ester derivative and lithium aluminium hydride (1 M in THF, 9.4 ml, 9.4 mmol) were carefully combined under a nitrogen atmosphere and following addition were heated to reflux. After 5 h the reaction was cooled to room temperature and carefully quenched using dropwise water addition with ice cooling, then filtered and washed with dichloromethane. The solvent was evaporated to give 3-(hydroxymethyl)morpholine (409 mg). EIMS: m/z=118.2 (M+H)$^+$.

To a solution of 3-(hydroxymethyl)morpholine (345 mg; 2.95 mmol) in dichloromethane (10 mL) was carefully added 2-fluorobenzoyl chloride (0.35 mL; 2.95 mmol) and triethylamine (0.62 mL; 4.42 mmol) and the reaction stirred for 0.5 h. The product was combined with 4 N NaOH (10 mL) to hydrolyse any ester and the organic layer extracted (dichloromethane, 3×). The combined organic layers were dried (Na$_2$SO$_4$) and the solvent evaporated to give an oil, which was purified by flash column chromatography on silica (gradient elution, dichloromethane-methanol 1:0 to 9:1) to give 4-(2-fluorobenzoyl)-3-(hydroxymethyl)morpholine (165 mg; 0.69 mmol), EIMS: m/z=240.2 (M+H)$^+$. This product and caesium carbonate (0.544 g) were heated to 120° C. in dimethylformamide (10 ml) solution under nitrogen for 4 hours. The solvent was evaporated, and the residue taken up in water and extracted with dichloromethane (3×). The combined dichloromethane extracts were dried (Na$_2$SO$_4$) and the solvent evaporated to give a crude solid which was purified by flash column chromatography on silica, eluting with ether to give the title compound (77 mg). M.p. 105-107° C.; EIMS: m/z=220.2 (M+H)$^+$.

4EXAMPLE 23

(S)-1,2,10,10a-Tetrahydroazetidinyl[2,1-c][1,4]benzoxazepin-4-one

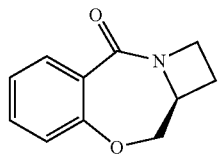

N-Methylmorpholine (1.35 ml, 12 mmol) was added to a stirred solution of (S)-azetidine-2-carboxylic acid (1.08 g; 10 mmol) and di-tert-butyl-dicarbonate (3.03 g; 14 mmol) in 1,4-dioxane: water (1:1, 30 ml) cooled to 0° C. The system was allowed to stir for 18 h with the temperature being allowed to rise slowly to room temperature. Saturated sodium bicarbonate solution (15 ml), cooled to 5° C. was added and the system was washed with ethyl acetate (3×75 ml). The aqueous phase was then acidified to pH 3 by the addition of potassium hydrogen sulfate. The aqueous phase was then extracted with ethyl acetate (3×100 ml), these organic layers were combined, dried (MgSO$_4$), filtered and solvent removed in vacuo to give the product (S)-N-teft-butoxycarbonyl-azetidine-2-carboxylic acid (2.15 g) as a viscous oil. EIMS:

m/z=201 (M+H)+Borane-THF complex (1M sol, 35 ml, 35 mmol) was added slowly to a stirred solution of the above carboxylic acid in dry tetrahydrofuran cooled to <5° C. under nitrogen. The reaction was allowed to stir for 18 h, with the temperature being allowed to slowly rise to room temperature. 10% Aqueous potassium hydrogen sulfate (10 ml) was then added dropwise. Volatile components were evaporated in vacuo and the remaining slurry was extracted with ethyl acetate (3×75 ml). The combined organic phase was dried (MgSO$_4$), filtered and solvent removed in vacuo to give the product (S)-N-tert-Butoxycarbonyl-2-hydroxymethylazetidine as a viscous oil (1.48 g, 74%), m/z [M+Na]$^+$ 210.

Trifluoroacetic acid (5 ml) in dichloromethane (5 ml) was added to a stirred solution of (S)-N-tert-butoxycarbonyl-azetidin-2-ylmethanol (1.17 g, 6.25 mmol) in dichloromethane (8 ml) cooled to [5° C. under nitrogen. The reaction was stirred for 18 h with the temperature being allowed to rise slowly to RT. Solvent and excess acid were removed in vacuo to give the product (S)-2-hydroxymethylazetidine, trifluoroacetate salt as a viscous oil (1.26 g). Triethylamine (0.61 ml, 4.38 mmol) was added slowly to a solution of 0.19 g of (S)-2-hydroxymethylazetidine trifluoroacetate salt (0.94 mmol) and 2-fluorobenzoyl chloride (0.16 ml, 1.30 mmol) in dichloromethane (8 ml) cooled to ~5° C. and under nitrogen. The reaction was stirred for 18 h with the temperature being allowed to rise slowly to room temperature. Water (15 ml) and dichloromethane (20 ml) were added and the layers were separated. The aqueous layer was washed with more dichloromethane (20 ml) and the combined organic layers were dried (MgSO$_4$), filtered and solvent removed in vacuo. The crude residue was purified by chromatography on silica gel using ethyl acetate:petroleum ether (40/60) 1:1, as eluant giving (S)-N-(2-fluorobenzoyl)-2-hydroxymethylazetidine (0.15 g; 0.72 mmol) as a viscous oil, EIMS: m/z=192 f(M+H)-H$_2$O]$^+$ The crude product was dissolved in dry dimethylformamide (5 ml) and anhydrous caesium carbonate (0.28 g, 0.87 mmol) was added to the stirred solution. The temperature was increased to 110° C. and the reaction was stirred for 18 h. After cooling, dimethylformamide was removed in vacuo. The residue was then taken up in water (20 ml) and extracted with dichloromethane (2×25 ml). The combined organic layers were dried (MgSO$_4$), filtered and solvent removed in vacuo. The crude residue was purified by chromatography on silica gel using ethyl acetate:petroleum ether (40/60) 4:1, as eluant, giving the title product (50 mg) as a white solid. M. p. 148-149° C.; $^1$H NMR (400 MHz; CDCl$_3$) δ 2.1-2.17 (m, 2H), 2.54-2.58 (m, 2H), 4.07-4.16 (m, 1H), 4.19 (dd, 1H), 4.28-4.32 (m, 1H), 4.45 (dd, 1H), 4.65-4.79 (m, 1H), 6.97 (d, 1H), 7.05 (dd, 1H), 7.38 (ddd, 1H), 8.11 (dd, 1H); EIMS: m/z=190 [M+H]$^+$

EXAMPLE 24

2,11,11a-Trihydro-3,3dimethyloxazolidinyl[2,1-c][1,4]-benzoxazepin-5-one

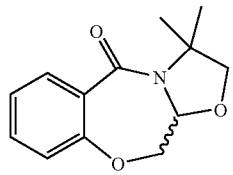

2-Amino-2-methyl-1-propanol (9.54 ml, 0.10 mol) was added to a stirred solution of ethyl glyoxylate (50% soln. in toluene, 21 ml, 0.10 mol) in dichloromethane (100 ml) in the presence of 4 Å molecular sieves. The reaction was stirred under nitrogen for 16 h whereupon the system was filtered through Dicalite® and washed with more dichloromethane. Evaporation of the solvent in vacuo gave (1,1-dimethyl-2-hydroxy-ethylimino)-acetic acid ethyl ester (17.0 g) as an oil (EIMS: m/z=174 [M+H]$^+$). 2-Fluorobenzoyl chloride (0.60 ml, 5.00 mmol) and then pyridine (0.96 ml, 12.0 mmol) were added to a stirred solution of the above described ethyl ester (0.87 g, 5.00 mmol) in dichloromethane (8 ml) cooled to ~5° C. and under nitrogen. After 1.5 h water (20 ml) was added, the layers separated and the aqueous phase washed with more dichloromethane (30 ml). The combined organic phase was then washed with 1N hydrochloric acid (25 ml) before being dried (MgSO$_4$), filtered and solvent removed in vacuo. The crude residue was purified by chromatography on silica using dichloromethane as eluant, to give 3-(2-fluorobenzoyl)-4,4-dimethyl-oxazolidine-2-carboxylic acid ethyl ester (0.64 g) as an oil, EIMS: m/z=296 [M+H]$^+$ Excess lithium borohydride was added to a stirred solution of 3-(2-fluorobenzoyl)-4,4-dimethyl-oxazolidine-2-carboxy acid ethyl ester (0.47 g; 1.58 mmol) in dry diethylether (5 ml). Dry toluene (8 ml) was then added and the system was heated to 100° C. After 2 h, the diethylether was distilled off as described by H. C. Brown et al (*J. Org. Chem.*, 1982, 47(24), 4702). After 6 h heating, the system was allowed to cool and then the toluene was removed in vacuo. Aqueous acid (5N HCl:H$_2$O=1:3 v/v; 8 ml) was then added and the system was stirred at room temperature for 1 h. Potassium carbonate was then added to saturate the aqueous solution which was then extracted with diethylether (2×25 ml). The combined organic layers were dried (MgSO$_4$), filtered and solvent removed in vacuo. The crude residue was purified by chromatography on silica gel using dichloromethane:methanol 19:1 as eluant. This gave (±)-3-(2-fluorobenzoyl)-4,4-dimethyl-2-hydroxymethyl-oxazolidine (0.30 g) as a viscous oil, EIMS: m/z=254 [M+H]$^+$ Caesium carbonate (0.60 g, 1.85 mmol) was added to a stirred solution of the above described oxazolidine (0.31 g, 1.23 mmol) in dry dimethylformamide (5 ml). The reaction mixture was heated to 130° C. and stirred for 18 h. After cooling, dimethylformamide was removed in vacuo, water (10 ml) was added to the residue which was then extracted with dichloromethane (3×30 ml). The combined organic layers were dried (MgSO$_4$), filtered and solvent removed in vacuo. The crude residue was purified by chromatography on silica gel using petroleum ether (40/60): ethyl acetate 4:1 (v/v) as eluent to give the title product (0.23 g) as a white waxy solid. M.p. 65.5-66.5° C. ° C.; $^1$H NMR (400 MHz; CDCl$_3$) δ 1.59 (s, 3H), 1.64 (s, 3H), 3.76 (d, 1H), 3.90 (d, 1H), 4.02 (dd, 1H), 4.54 (dd, 1H), 5.18 (dd, 1H), 6.96 (d, 1H), 7.08 (ddd, 1H), 7.36 (ddd, 1H), 8.06 (dd, 1H); EIMS: m/z=234 [M+H]$^+$

EXAMPLE 25

(2R,11aS)-2-Hydroxy-2,3,11,11a-tetrahydro-1H,5H-pyrrolo[2,1-c][1,4]benzoxazepine-5-one

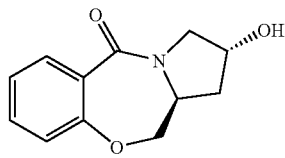

To a stirred slurry of (3R, 5,S)-3-hydroxy-5-hydroxymethylpyrrolidine (3.67 g; 23.9 mmol) (M. W. Reed et al, *J. Med. Chem.*, 1995, 38, 4587-4596) and diisopropylethylamine (9.3 ml; 52.58 mmol) in anhydrous dichloromethane (30 ml) under a nitrogen atmosphere was added dropwise 2-fluorobenzoylchloride (3.8 g; 23.9 mmol) while maintaining the temperature below 25° C. by means of an ice bath. The mixture was allowed to stir at room temperature overnight and then evaporated under reduced pressure. The resultant mixture was taken up in ethyl acetate (100 ml), washed with water (2×50 ml) and dried (Na$_2$SO$_4$). The solvent was evaporated under reduced pressure and the residue purified by flash chromatography eluenting with 1:9 methanol in dichloromethane to give the intermediate amide (5.2 g) as a colourless oil, EIMS: m/z=240.2 [M+H]$^+$. This amide (21.76 mmol) was suspended in dimethylformamide (70 ml) and caesium carbonate (8.5 g; 26.1 mmol) was added and the suspension was stirred under a nitrogen atmosphere at 110° C. for 16 hrs. The mixture was then evaporated to dryness under reduced pressure and the residue was then taken up in 100 ml of ethyl acetate. The solution was washed with water (80 ml) and the water layer then re-extracted with further ethyl acetate (100 ml). The combined organic extracts were then washed with brine (2×50 ml) and dried Na$_2$SO$_4$). The solvent was evaporated under reduced pressure and the residue further purified by flash chromatography eluting with 7% MeOH in methylene chloride to give the title compound (2.2 g) as a white crystalline solid. $^1$H NMR (400 MHz; CDCl$_3$) δ 2.75 to 2.87 (m, 1H), 2.02 (d, 1H), 2.2 to 2.30 (m, 1H), 3.857 (d, 2H), 4.03 to 4.07 (m, 1H), 4.24 (q, 1H), 4.48 (d, 1H), 4.55 (s, 1H), 6.97 (d, 1H), 7.06 (t, 1H), 7.36 (t, 1H), 8.109 (t, 1H); EIMS: m/z=220.2 [M+H]$^+$

EXAMPLE 26

(2S,11aS)2-Fluoro-23,11,11a-tetrahydro-1H,5H-pyrrolo[2,1-c][1,4]benzoxazepine-5-one

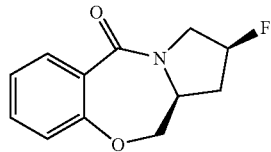

A solution of the material prepared in Example 25 (200 mg; 0.91 mmol) in dry ethyl acetate (10 ml) was cooled to −50° C. and (diethylamino)sulphur trifluoride (191 mg; 1.19 mmol) was added dropwise. The resultant solution was stirred at −50° C. for 1 h and then allowed to slowly warm to room temperature over a period of 3 h. The mixture was then poured onto a saturated aqueous NaHCO$_3$ solution (50 ml) and further ethyl acetate (50 ml) added. After thorough mixing the organic layer was separated, washed sequentially with water (50 ml) and brine (50 ml), and dried (Na$_2$SO$_4$). The solvent was evaporated under reduced pressure and the residue was purified by flash chromatography to give the title compound as a pale yellow crystalline solid (60 mg). $^1$H NMR (CDCl$_3$) δ 2.13 to 2.48 (m, 2H), 3.79 (qd, 1H), 4.09 (t, 1H), 4.25 to 4.35 (m, 2H), 4.43-4.49 (m, 1H), 5.333 (d, 1H), 7.04 (d, 1H), 7.15 (t, 1H), 7.41 (dd, 1H), 7.88 (dd, 1H); EIMS: m/z=222.2 [M+H]$^+$

EXAMPLE 27

(S)-2-Oxo-2,3,11,11a-tetrahydro-1H,5H-pyrrolo[2,1-c][1,4]benzoxazepine-5-one

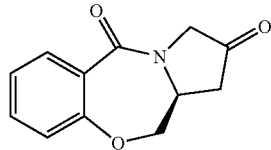

To a stirred solution of oxalyl chloride (0.52 ml; 5.94 mmol) in dry dichloromethane (15 ml) cooled to −78° C. was added a solution of dimethylsulfoxide (0.81 ml, 11.42 mmol) in dry dichloromethane (2 ml). Stirring was continued for 10 minutes followed by dropwise addition of a solution of the material (1 g) prepared in Example 25 (4.57 mmol) in dry dichloromethane (10 ml). The mixture was stirred for a further 15 minutes then triethylamine (3.8 ml; 27.3 mmol) was added. After stirring at −78° C. for a further 10 minutes the mixture was allowed to warm to 0° C. before ethyl acetate (50 ml) and water (50 ml) were added. After thorough mixing the organic layer was separated, washed sequentially with 1M HCl (50 ml) and brine (50 ml), and dried (Na$_2$SO$_4$). The solvent was removed under reduced pressure and the residue purified by flash chromatography eluting with 3% MeOH in methylene chloride to give the title product (220 mg) which was recrystallised once from the minimum of hot ethyl acetate, $^1$H NMR (CDCl$_3$) δ 2.41 (dd, 1H), 2.87-2.93 (m, 1H), 4.15-4.33 (m, 3H), 4.45-4.49 (m, 2H), 7.06 (d, 1H), 7.18 (t, 1H), 7.44 (dd, 1H), 8.03 (dd, 1H); EIMS: m/z=218.4 [M+H]$^+$

EXAMPLE 28

(2S)-2,2-Difluoro-2,3,11,11a-tetrahydro-1H,5H-pyrrolo[2,1-c][1,4]benzoxazepine-5-one

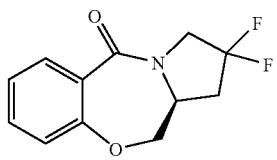

To a solution of the material prepared in Example 27 in methylene chloride (5 ml) was added diethylaminosulfur trifluoride ((245 mg; 1.5 mmol). The reaction was stirred for 2 days at room temperature then quenched by the addition of ice and washed with water (10 ml) and saturated sodium bicarbonate solution (10 ml) and dried (Na$_2$SO$_4$). Evaporation and purification by flash chromatography eluting with 19:1 methylene chloride-ether afforded the title compound as an off-white solid (63 mg). M.p. 116-5-119.5° C.; EIMS: m/z=240.0 [M+H]$^+$

EXAMPLE 29

Patch Clamp Whole Cell Electrophysiology

A: Cell Culture.

Hippocampal neurons were prepared from embryonic or 1-3 day old Sprague-Dawley rats which were decapitated and the heads immediately placed in ice cold HBS (HEPES Buffered Solution: 130 mM NaCl, 5.4 mM KCl, 10 mM HEPES, 1.0 mM MgCl$_2$, 1.8 CaCl$_2$, 25 mM glucose, adjusted to pH 7.4). The whole brain was excised and placed on pre-sterilised filter paper, soaked in HBS and the cerebellum was removed. The brain was chopped and an enzyme solution (0.5 mg/ml protease X and 0.5 mg/ml protease in HBS) was added and subsequently left for 40 minutes at room temperature to digest before trituration. Cells were resuspended and then counted to give a final concentration of 1.5×10$^8$ per ml. Cells were aliquoted onto poly-D-lysine- and Matrigel®-treated coverslips and left to incubate at 37° C. for 1-2 hours. When incubation was complete, 1 ml of growth medium was added to each well containing a coverslip and the cells were returned to the incubator. After 3-5 days the mitotic inhibitor cytosine arabinoside (5 μM) was added and the cells returned to the incubator until required.

B: Patch Clamp Recording.

The whole cell configuration of the patch clamp technique (Hamill et al., *Pflügers Arch.* 1981, 39, 85-100) was used to measure glutamate-evoked currents from postnatal hippocampal neurons maintained in culture for 4-7 days. A glass coverslip containing the culture was transferred to the recording chamber (Warner Instrument Corp., Hamden, Conn.) mounted on the stage of an inverted microscope (Nikon, Kingston, UK). The recording chamber contained 1-2 ml extracellular solution (145 mM NaCl, 5.4 mM KCl, 10 mM HEPES, 0.8 mM $MgCl_2$, 1.8 $CaCl_2$, 10 mM glucose and 30 mM sucrose, adjusted to pH 7.4 with 1M NaOH) and was constantly perfused at a rate of 1 ml/min. Recordings were performed at room temperature (20-22° C.) using an Axopatch 200B amplifier (Axon Instruments Ltd., Foster City, Calif.). Data acquisition and analysis was performed using Signal software (Cambridge electronic Design Ltd., Cambridge, UK). Pipettes were manufactured from GC120F-10 glass (Harvard Apparatus, Edenbridge UK) using a model P-87 electrode puller (Sutter Instruments Co., Novarto, Calif.). The patch electrodes had typical resistances of between 3-5 MΩ when filled with intracellular solution (140 mM potassium gluconate, 20 mM HEPES, 10 mM EGTA, 5 mM phosphocreatine, 3 mM ATP, 0.3 mM GTP, 0.1 mM $CaCl_2$, 5 mM $MgCl_2$, adjusted to pH 7.4 with 1M KOH).

Cells were voltage clamped at a holding potential of −60 mV and glutamate (0.5 mM) was applied using a 12 channel semi-rapid drug application device (DAD-12. Digitimer Ltd., Welwyn Garden City, UK). The agonist glutamate was applied for 1 s every 30 s. The response did not "run-down" over time using the whole-cell configuration. Between applications saline flowed to clear any dead volume in the system. For each application steady-state currents were plotted from the difference in baseline and steady state current and averaged over 300 ms.

Two solutions of the compound in extracellular solution were made up, one with glutamate and one without. The protocol was: 10 second application of compound, 1 second application of compound+glutamate and then 10 second wash with saline, then a 10 second delay. When the compound was not soluble, 0.5% DMSO was used as a co-solvent. Results are presented in Table I as the percentage increase in steady state current at 10 μM concentration of the compound of the invention in extracellular solution.

EXAMPLE 30

Differential Reinforcement of Low Rates of Responding, 72 Seconds (DRL72)

Rats are pretrained in a standard operant chamber to perform a DRL72 procedure according to Andrews et al (Andrews J S, Jansen J H M, Linders S, Princen A, Drinkenburg W H I M, Coenders C J H and Vossen J H M (1994). Effects of imipramine and mirtazapine on operant performance in rats. Drug Development Research, 32:58-66). The test session lasts for 60 minutes with no limit to the number of trials. Each trial begins with the stimulus light on above the active lever. A response on the lever only results in delivery of a pellet if 72 seconds has elapsed. A response on the lever before 72 seconds has elapsed resets the timer and is not rewarded. The number of pellets earned and the number of lever presses is recorded and used to calculate an efficiency score. Test compounds are administered via the intraperitoneal route 30 minutes before the start of the test session. Antidepressants increase the number of pellets earned and decrease the number of lever presses (Andrews et al, 1994). (S)-9-Fluoro-2,3,11,11a-tetrahydro-1H,5H-pyrrolo[2,1-c] [1,4]benzoxazepine-5-one (Example 3B exhibited an antidepressant like profile.

EXAMPLE 31

Inhibition of Amphetamine-induced Hyperlocomotion.

Mice were injected sc with drug or vehicle control. 30 Minutes later mice were injected sc with 1.5 mg/kg d-amphetamine sulphate or saline and immediately placed in infra red locomotor boxes where locomotor activity (long duration beam breaks of two adjacent beams) and stereotypic behaviour (repetitive short-duration beam breaks) were measured for a period of 60 minutes. The experiment was analysed using a 3-Way ANOVA with experimental session, infra red locomotor boxes and treatment as factors, and in the case of treatment, significant effects were followed up using a Tukey (HSD) test. (S)-2,3,11,11a-tetrahydro-1H,5H-pyrrolo[2,1-c] [1,4]-benzoxazepine-5-on and (R)-9-fluoro-2,3,11,11a-tetrahydro-1H,5H-pyrrolo[2,1-c][1,4]benzoxazepine-5-one (Example 3A showed antipsychotic like activity as shown by inhibited amphetamine induced hyperlocomotion.

TABLE I

| Compound | % Increase In steady state current at 10 μM |
| --- | --- |
| (S)-2,3,11,11a-tetrahydro-1H,5H-pyrrolo[2,1-c][1,4]benzoxazepine-5-one* | 53 |
| (R)-2,3,11,11a-tetrahydro-1H,5H-pyrrolo[2,1-c][1,4]benzoxazepine-5-one | 24 |
| (R)-7-Fluoro-2,3,11,11a-tetrahydro-1H,5H-pyrrolo[2,1-c][1,4]-benzoxazepine-5-one (Example 1) | 17 |
| (S)-7-Fluoro-2,3,11,11a-tetrahydro-1H,5H-pyrrolo[2,1-c][1,4]-benzoxazepine-5-one (Example 2) | 19 |
| (R)-9-Fluoro-2,3,11,11a-tetrahydro-1H,5H-pyrrolo[2,1-c][1,4]-benzoxazepine-5-one (Example 3A) | 23 |
| (S)-9-Fluoro-2,3,11,11a-tetrahydro-1H,5H-pyrrolo[2,1-c][1,4]-benzoxazepine-5-one (Example 3B) | 20 |
| (S)-2,3,11,11a-tetrahydro-1H,5H-pyrrolo[2,1-c][5,1,4]benzthiaoxazepine-5-dioxide (Example 10) | 7 |
| (S)-8-Methoxy-2,3,11,11a-tetrahydro-1H,5H-pyrrolo-[2,1-c][1,4]benzoxazepine-5-one (Example 11) | 21 |
| (S)-N-(2,3,11,11a-tetrahydro-5-oxo-1H,5H-pyrrolo[2,1-a][1,4]benzoxazepin-7-yl)acetamide (Example 14) | 49 |

TABLE I-continued

| Compound | % Increase In steady state current at 10 μM |
|---|---|
| (S)-7-(morpholinocarbonyl)-2,3,11,11a-tetrahydro-1H,5H-pyrrolo[2,1-c][1,4]benzoxazepine-5-one (Example 16A) | 24 |
| (R)-7-(aminocarbonyl)-2,3,11,11a-tetrahydro-1H,5H-pyrrolo[2,1-c][1,4]benzoxazepine-5-one (Example 17A) | 8 |
| (11R,11aS)-11-Ethyl-2,3,11,11a-tetrahydro-1H,5H-pyrrolo[2,1-c][1,4]benzoxazepine-5-one (Example 20A) | 31 |
| (11S,11aS)-11-Ethyl-2,3,11,11a-tetrahydro-1H,5H-pyrrolo[2,1-c][1,4]benzoxazepine-5-one (Example 20B) | 28 |
| 6,6a-Dihydro-12H-Morpholino[3,4-c][1,4]benzoxazepin-12-one (Example 22) | 31 |
| (S)-1,2,10,10a-Tetrahydroazetidinyl[2,1-c][1,4]benzoxazepin-4-one (Example 23) | 16 |
| 2,11,11a-Trihydro-3,3-dimethyloxazolidinyl[2,1-c][1,4]-benzoxazepin-5-one (Example 24) | 18 |
| (2R,11aS)-2-Hydroxy-2,3,11,11a-tetrahydro-1H,5H-pyrrolo[2,1-c][1,4]benzoxazepine-5-one (Example 25) | 31 |
| (2S,11aS)-2-Fluoro-2,3,11,11a-tetrahydro-1H,5H-pyrrolo[2,1-c][1,4]benzoxazepine-5-one (Example 26) | 24 |
| (2S,11aS)-2,2-Difluoro-2,3,11,11a-tetrahydro-1H,5H-pyrrolo[2,1-c][1,4]benzoxazepine-5-one (Example 28) | 9 |

*this compound was prepared as described by Schultz, A. G. et al (J. Am. Chem Soc. 1988, 110, 7828-7841) who use the naming: (3aS)-2,3,3a,4-tetrahydro-1H,1H-pyrrolo[2,1-c]benzoxazepin-10-one.

We claim:

1. A pharmaceutical composition, comprising:
a benzoxazepine compound of formula I

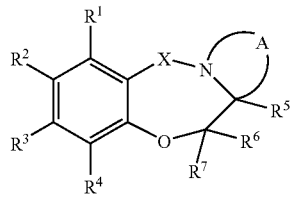

Formula I wherein X represents CO or $SO_2$;
$R^1$, $R^2$, $R^3$ and $R^4$ are independently selected from H, $(C_{1-4})$alkyl, $(C_{1-4})$alkyloxy, $(C_{1-4})$alkyloxy$(C_{1-4})$alkyl, $CF_3$, halogen, nitro, cyano, $NR^8R^9$, $NR^8COR^{10}$, and $CONR^8R^9$;
$R^5$, $R^6$ and $R^7$ are independently H or $(C_{1-4})$alkyl;
$R^8$ and $R^9$ are independently H or $(C_{1-4})$alkyl; or $R^8$ and $R^9$ form together with the nitrogen atom to which they are bound a 5- or 6-membered saturated heterocyclic ring, optionally containing a further heteroatom selected from O, S or $NR^{11}$;
$R^{10}$ is $(C_{1-4})$alkyl;
$R^{11}$ is $(C_{1-4})$alkyl;
A represents a $C_{2-5}$ alkylene forming a saturated heterocyclic ring, wherein a carbon atom may be replaced by an oxygen atom, ring being optionally substituted with 1-3 substituents selected from $(C_{1-4})$alkyl, $(C_{1-4})$alkyloxy, hydroxy, halogen and oxo; or a pharmaceutically acceptable salt thereof, and a pharmaceutically acceptable carrier.

2. A method of treating a neurological disease or a psychiatric disorder in a patient, wherein the disease or disorder is selected from the group consisting of schizophrenia, depression and cognitive or memory dysfunction, the method comprising:
administering a therapeutically effective amount of a benzoxazepine compound according to Formula I

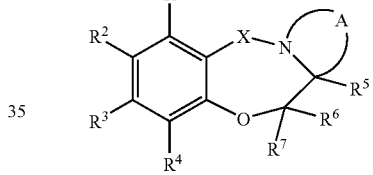

Formula I wherein X represents CO or $SO_2$;
$R^1$, $R^2$, $R^3$ and $R^4$ are independently selected from H, $(C_{1-4})$alkyl, $(C_{1-4})$alkyloxy, $(C_{1-4})$alkyloxy$(C_{1-4})$alkyl, $CF_3$, halogen, nitro, cyano, $NR^8R^9$, $NR^8COR^{10}$, and $CONR^8R^9$;
$R^5$, $R^6$ and $R^7$ are independently H or $(C_{1-4})$alkyl;
$R^8$ and $R^9$ are independently H or $(C_{1-4})$alkyl; or $R^8$ and $R^9$ form together with the nitrogen atom to which they are bound a 5- or 6-membered saturated heterocyclic ring, optionally containing a further heteroatom selected from O, S or $NR^{11}$;
$R^{10}$ is $(C_{1-4})$alkyl;
$R^{11}$ is $(C_{1-4})$alkyl;
A represents a $C_{2-5}$ alkylene forming a saturated heterocyclic ring, wherein a carbon atom may be replaced by an oxygen atom, the ring being optionally substituted with 1-3 substituents selected from $(C_{1-4})$alkyl, $(C_{1-4})$alkyloxy, hydroxy, halogen and oxo; or a pharmaceutically acceptable salt thereof.

3. The method according to claim 2, wherein the disease or disorder is cognitive or memory dysfunction.

4. The method according to claim 2, wherein the disease or disorder is schizophrenia.

5. The method according to claim 2, wherein the disease or disorder is depression.

* * * * *